United States Patent [19]
Haushalter et al.

[11] Patent Number: 5,324,848
[45] Date of Patent: Jun. 28, 1994

[54] VANADIUM PHOSPHATE MATERIALS

[75] Inventors: Robert C. Haushalter, Little York; Victoria G. Soghomonian, Princeton, both of N.J.; Jon A. Zubieta, Syracuse, N.Y.

[73] Assignee: NEC Research Institute, Inc., Princeton, N.J.

[21] Appl. No.: 29,444

[22] Filed: Mar. 11, 1993

[51] Int. Cl.$^5$ ............................................... C07F 9/02
[52] U.S. Cl. ...................................... 556/13; 556/17; 556/26; 556/42
[58] Field of Search .................. 556/13, 26, 17, 42

[56] References Cited

U.S. PATENT DOCUMENTS 4,956,483  9/1990  Corcoran, Jr. et al. ............... 556/26
5,200,187  4/1993  Haushalter et al. ................. 423/308

OTHER PUBLICATIONS

Soghomonian et al., Science, vol. 259, pp. 1596–1599 (1993).

Primary Examiner—Paul J. Killos
Assistant Examiner—Porfirio Nazario-Gonzalez
Attorney, Agent, or Firm—Arthur J. Torsiglieri

[57] ABSTRACT

A new class of vanadium phosphate materials has been created using hydrothermanl self-assembly techniques. Of particular interest is that these materials comprise a vanadium phosphate framework structure about an organic template that after removal leave a microporous structure. These materials typically are produced by a reaction in an aqueous solution that includes one or more phosphate sources, one or more vanadium or vanadium oxide sources, an alkali metal or alkali-earth metal sources, and an organic amine or diamine templating agent.

17 Claims, 6 Drawing Sheets

VANADIUM PHOSPHATE MATERIALS

FIELD OF INVENTION

This invention relates to novel vanadium phosphate materials useful to provide microporous structures and to the methods for the preparation of such materials.

BACKGROUND OF THE INVENTION

There is currently intense interest in the chemistry of the vanadium oxide phosphate system because the system is capable of providing networks of connected vanadium and phosphorus polyhedra with a diversity of structures. This structural diversity is associated in part with the ability of vanadium oxygen coordination polyhedra to adopt tetrahedral, square pyramidal and octahedral geometries and to aggregate into larger cores by condensation of polyhedra through shared oxygen atoms. Further condensation with phosphate tetrahedra, such as $PO_4^{3-}$, $HPO_4^{2-}$ and $H_2PO_4^{-1}$ results often in complex polyhedral networks.

Moreover, when cationic templates are introduced, polyhedral framework solids with tunnels, cages and micropores may be isolated. Such solids offer considerable promise since they make possible microporous framework solids, capable of shape selective absorption like the zeolites and aluminophosphates, that are useful as catalysts or molecular sieves.

Generally in the past with vanadium oxide phosphate systems, such templates have involved inorganic materials but the use of such materials has limited the size and shape of the micropores that can be realized. Of greater potential interest would be framework structures that could be assembled about templates of large size organic molecules that could later be removed, either by ion exchange or thermal methods, to leave pores of size comparable to those of the organic template molecules.

To this end, recently, hydrothermal self-assembly syntheses have been used to prepare microporous, octahedral framework molydenum phosphates formed about organic cationic templates, but these molydenum phosphate frameworks with organic cationic templates are of restricted applicability and there is interest in structures involving other metal phosphate compositions, such as vanadium phosphates, to increase the range of options.

SUMMARY OF THE INVENTION

An object of the present invention is a vanadium phosphate crystalline material that can be formed hydrothermally by self assembly of ordered arrays about a template of organic molecules such that when the template is removed from the framework there remains a vanadium phosphate framework with micropores of size and shape adapted to sorb desired molecules.

To this end, the invention provides novel crystalline vanadium phosphate compositions that can be made microporous and that can advantageously be prepared by the self assembly of structurally simple precursors. The compositions of the invention are embraced within the generic formula where A is one or more metals chosen from the group of alkali metals or alkaline-earth metals consisting of Li, Na, K, Rb, Cs, Mg, Ca, Sr, and Ba; B is an organic template of the form $R_4N$ in which R is one or more compositions chosen from the group consisting of H, $C_nH_{2n+1}$, $C_nH_{2n}NQ_3$ where n has a value equal to or less than 4 and Q is either H or $C_nH_{2n+1}$; and each of a and d has a value greater than zero, each of b, c, e, f, g, h, i, j, and x has a value equal to or greater than zero, but at least one of g, h and i has a value greater than zero.

The structure of such compositions, as determined by x-ray diffraction, can be grossly described as a three dimensional covalently bonded framework built up from $VO_6$ octahedra and/or $VO_5$ square pyramids, and phosphate tetrahedra, such as $PO_4^{3-}$, $HPO_4^{2-}$ and $H_2PO_4^{1-}$. For such structures species of alkylammonium or alkyldiammonium ions have proven of particular interest for use as a cationic organic template, but it is anticipated that other organic ions should also be able serve the same function.

One such composition is $K_4[(CH_3)_2NH_2][V_{10}O_{10}(OH)_4(PO_4)_7(H_2O)_2]\cdot 4H_2O$ (hereinafter composition (1)), and it is characterized by chiral double helices that are formed from interpenetrating spirals of vanadium oxo pentameters bonded together by $P^{5+}$ about a cationic organic template and the $K^+$ cation. The double helices are in turn intertwined with each other in a manner that generates voids that include relatively large tunnels that enclose dimethylammonium ions. This composition was prepared by hydrothermal treatment of a solution comprising various inorganic materials and organic dimethylamine which served to provide the template about which the vanadium phosphate structure was formed as a framework.

An example of a vanadium phosphate composition that was formed about an ethylenediammonium template material is hereinafter to be referred to as composition (2).

Other examples of vanadium phosphate compositions including organic templates that were obtained include $[H_3NCH_2CH_2CH_2NH_3][V_3O_3(OH)_2(PO_4)_2(H_2O)_2]$ to be designated as composition (3) and $K[H_3NCH_2CH_2CH_2NH_3][V_3O_3(PO_4)_3]$ to be designated as composition (4).

The invention will be better understood from the following more detailed specification taken with the accompanying drawings.

DETAILED DESCRIPTION OF THE INVENTION

A process that gave greater than 85 percent yield of monophasic, dark blue tetragonal pyramids of composition (1) was as follows. There was prepared a mixture of $KVO_3$, V, $H_3PO_4$, $CH_3PO_3H_2$, $(CH_3)_2NH$, and $H_2O$ in a mole ratio approximately of 2.35:1:10.2:3.3:8:1140 respectively, and it was maintained at about 200° C. for 4 days. The composition (1) was self-assembled. While the above set of conditions provided the highest yield, the growth process appeared not to be critically dependent on any particular parameter and yields in excess of fifty percent were obtained over a wide range of temperatures, times and mole ratios. Yield of at least fifty percent could be achieved when the $KVO_3$ was in the mole ratio range of between 1.48 and 2.37, the $H_3PO_4$ between 5.9 and 17.2, the $CH_3PO_3H_2$ between 2.43 and 5.9, the dimethylamine between 5.94 and 13.2 and the $H_2O$ between 500 and 1900. Also the heating could be done in the range between 185° C. and 235° C. and this range generally required times between 3 and 6 days for good yields. Excessively long periods tended to result in dissolution of the grown material. The cation template can be removed, leaving the vanadium phosphate framework, by heating, as for example to 650° C., in a heating step that reaches such temperature by increasing the temperature at the rate of about 10 degrees Centigrade a minute, typically in a nitrogen atmosphere. It also should be feasible to remove the cations by an appropriate ion exchange process.

It was also possible to make the same material with a yield of at least 50 percent with the following set of reagents, $KVO_3$, $V_2O_5$, V, $H_3PO_4$, DMA (dimethylamine), and $H_2O$ in approximately the following mole ratio, 0.67:0.83:1:1:0.13:222 respectively, and the DMA concentration could be increased to 0.26 with little effect.

Figure 1:
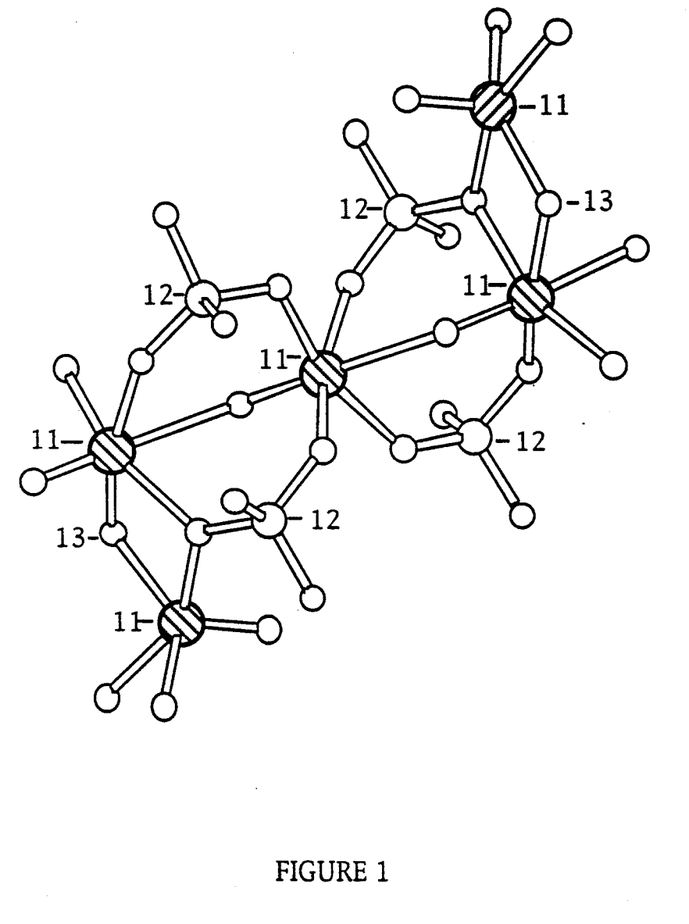
FIG. 1 shows the structure of one of the two structurally similar, crystallographically independent vanadium oxo pentameters.

The structure of composition (1) was determined by single-crystal x-ray diffraction and consists of a three-dimensional covalently bonded framework built up from $VO_6$ octahedra, $VO_5$ square pyramids, and $PO_4$ tetrahedra. Composition (1) crystallizes in the space group $P4_3$ (or its enantiomorph $P4_1$), and therefore the crystals are enantiomorphic and the unit cell contents are chiral. The fundamental building blocks are two structurally similar, crystallographically independent vanadium oxo pentamers, one of which is shown in FIG. 1. The pentameter includes the five vanadium atoms 11, the four phosphorus atoms 12, two hydroxyls 13 and the remainder (not numbered) oxygen atoms. Although each pentamer may appear to possess $\bar{1}$ symmetry, examination of the V—O distances shows that actually there is no symmetry present because of the alternation of long V—O (2.4 Å) and short V═O(1.7 Å) contacts along the seven-atom central V—O backbone of the pentamer. This backbone has a short V═O bond at one end and a long V—O bond to an $H_2O$ ligand at the other. The pentamers have a V—O—V backbone containing four V—O—V and two V—OH—V bonds. The connectivity is such that there is a central trimer of three $VO_6$ octahedra, with the central octahedron sharing trans corners with the two outer octahedra. Each of two outer octahedra of the trimer share an edge with two $VO_5$ square pyramids. These pentamers are arranged so as to form spirals, with four pentamers per spiral of unit cell length along [001].

Figure 2A:
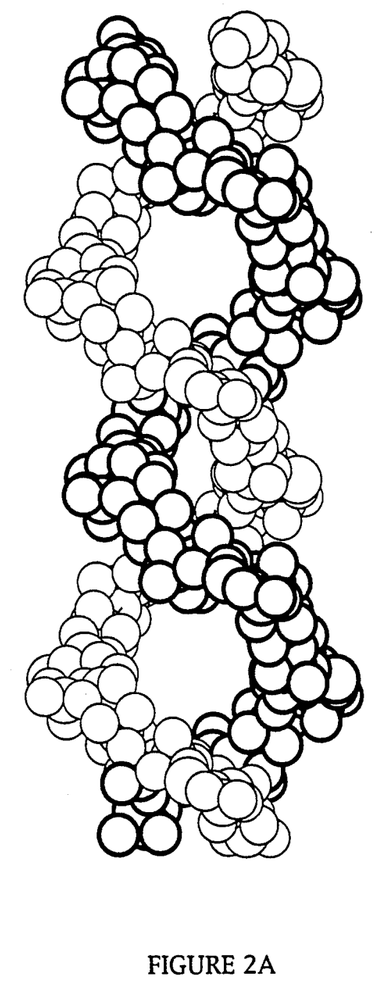
FIG. 2A and FIG. 2B each shows from a different angle perpendicular to the spiral axis a portion of the chiral double helix structure of composition (1) that forms one example of the invention.
Figure 2B:
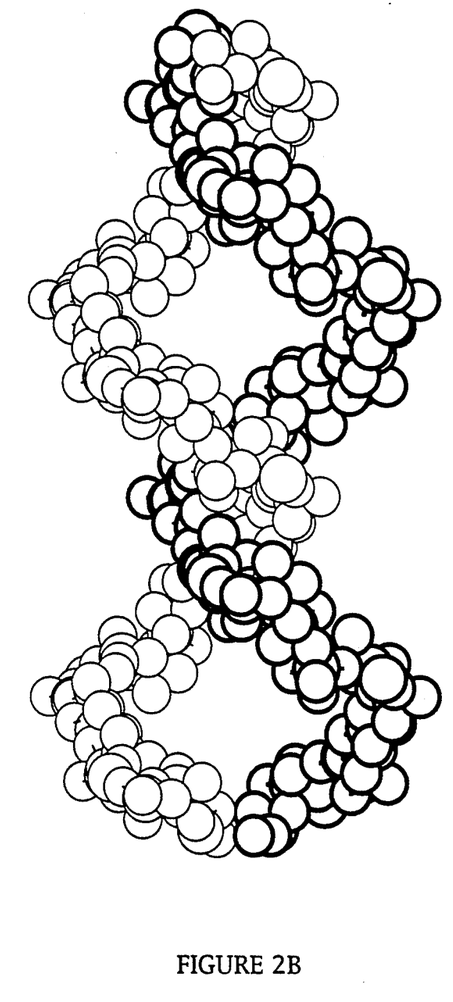

The spirals in turn are intertwined to give the two strands of a double helix as shown in FIG. 2A with one strand composed of V1–V5 and the other strand V6–V10. These helices are very unusual in that the two directions parallel to the axis of the helix are unequivalent and, because of the tetragonal space group, the helices appear to have a square cross section when viewed in projection down [001]. The perpendicular distance of the V—O backbone within the spiral to the central axis of the spiral varies as a function of the z axis coordinate of the unit cell, which results in what appears to be protruding major and minor loops when the helix is viewed from various angles perpendicular to the spiral axis (FIG. 2B). There are seven different types of phosphorus 5+ cations in the unit cell. Some P5+ serve to join the pentamers and some to connect the strands to one another to form the helix, whereas others bond one double helix to another.

Figure 3:
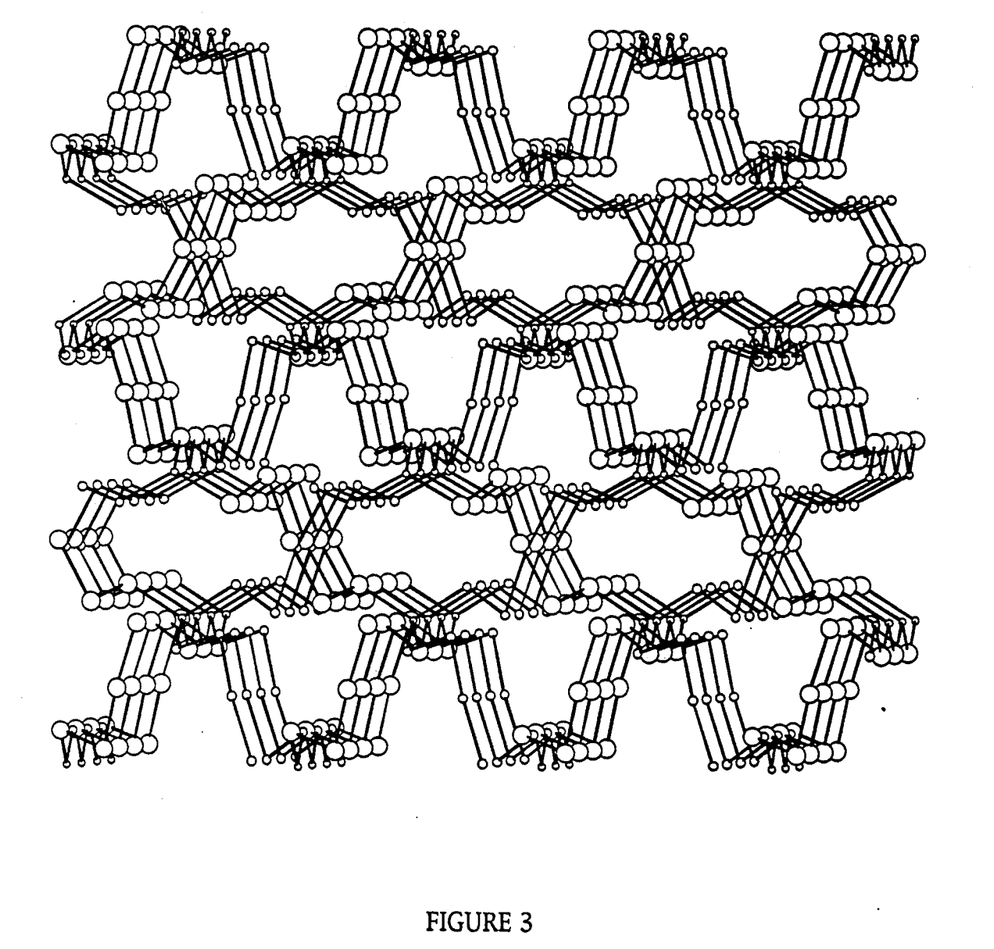
FIG. 3 illustrates schematically how the double helices shown in FIGS. 2A and 2B intergrow.

These strands and double helices intergrow with one another in an extremely complicated fashion as is illustrated schematically in FIG. 3. The essence of the symmetry is represented by the two sets of five unique V atoms and P1. The loops protruding from each double helix are quite large. Within a given unit cell, portions of the two crystallographically independent strands of each double helix undergo an excursion into the adjacent unit cells on either side of the original unit cell and then turn 90° and form the minor loop before returning to a point one unit cell translation in away but with the same x and y coordinates. When the helix forms the largest loops, another strand from another helix goes through the open loop. This interweaving of the strands and helicies gives rise to a three-dimensional array of interconnected braids.

Figure 4A:
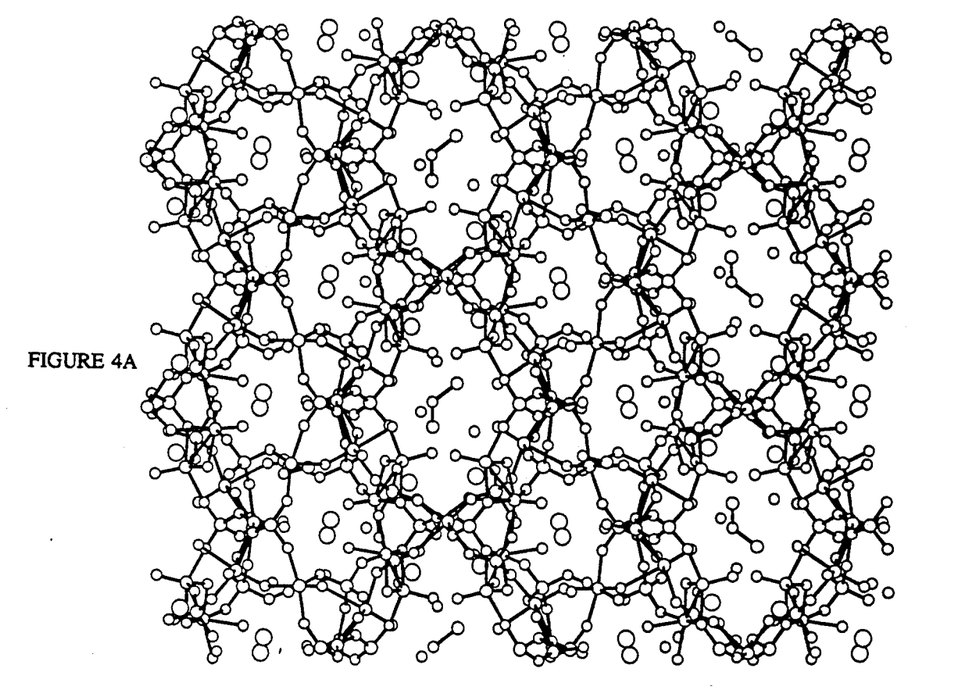
FIGS. 4A and 4B are projections of the unit cell contents parallel to the tetragonal a and b axes, respectively.
Figure 4B:
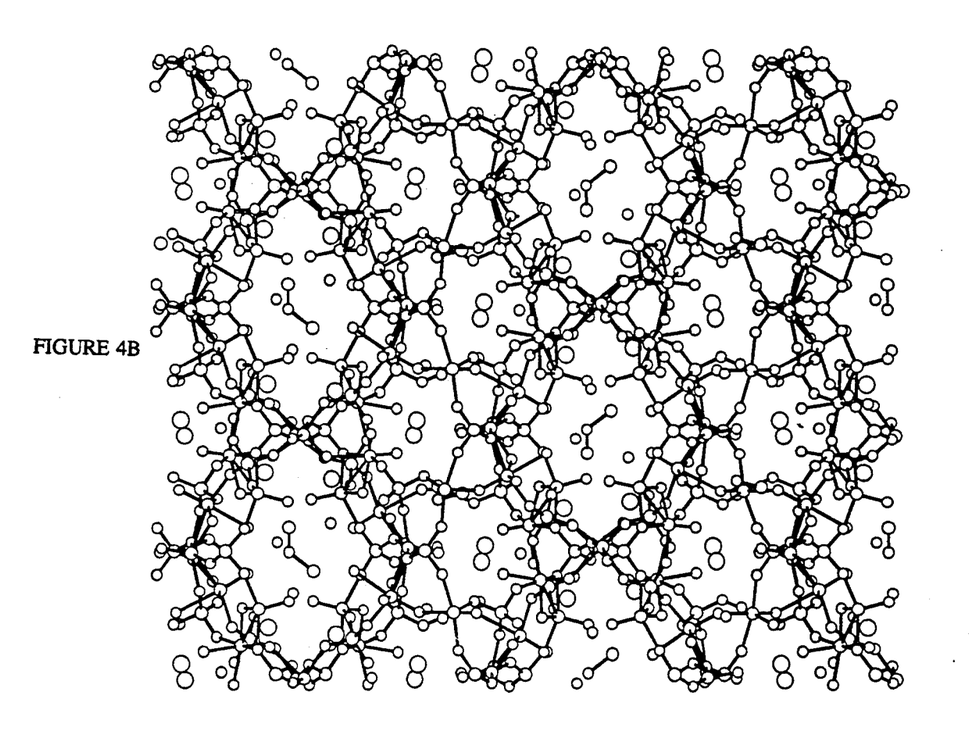

This connectivity of the covalently bonded vanadium phosphate framework generates relatively small cavities and a topologically unusual array of relatively large tunnels that contain the K+ and $(CH_3)_2NH_2^+$ cations, respectively. As shown in FIG. 4A and B, which are projections of the unit cell contents parallel to the tetragonal a and b axes, respectively, the tunnels that are filled with the dimethylammonium cations run parallel both to [100] at $\frac{1}{4}$ and $\frac{3}{4}$ in c axis and parallel to [010] at 0 and $\frac{1}{2}$, but at no point do the two types of tunnel intersect. In fact, the atoms that are the "ceiling" of one tunnel form the "floor" of the perpendicular tunnel above it. The shorter contacts of the less polar organic cations to the framework are the vanadyl (V═O) groups. The K+ cations lie in more polar regions of the structure and are coordinated to the solvate water. Based on the earlier observations in several molybdenum phosphates in which nonpolar organic cations were associated with less polar molybdenyl (Mo═O), regions of the framework and polar inorganic cations (e.g. Na+, $NH_4^+$, $H_3O^{30}$) were near the phosphate regions of the framework, we believe that hydrophobichydrophilic interactions are an important factor in understanding how these mixed organic-inorganic system crystallize.

Investigation of the magnetic properties of composition (1) shows that the material is paramagnetic at room temperature and that there are ten unpaired electrons per V10 formula unit consistent with the bond strength-bond length calculations, and characteristic of square pyramidal or distorted octahedral geometry of the vanadium, both of which indicate all ten V are $d^1$ $V^{4+}$. At lower temperatures there is a decrease in the magnetic moment of material (1), from 1.63 $\mu_B$ per V at room temperature to 1.01 $\mu_B$ at 2.5K, due to low dimensional antiferromagnetic interactions. The preparation of this open framework vanadium phosphate synthesized with organic templates that displays chirality suggests several possible applications, as in catalysis and as a molecular sieve. The tunnels in which the $(CH_3)_2N H_2^+$ cations reside are not exactly cylindrical and the atoms responsible for the minimum constrictions of 6.9 and 8.1 Å (atom-to-atom distances) do not define planes that are perpendicular to the axis of the tunnel. Some of the V atoms have potentially removable aquo ligands, which should provide shape-selective absorption. In particular, one can expect absorption or catalysis that would discriminate between enantiomers. All because composition (1) is a rare example of a material that is both chiral and strongly magnetic, it should have applications that depend on the existence of interactions between polarized light and an internal or external magnetic field.

Another example with different reagents included $V_2O_4$, $H_3PO_4$, KCl, DMA, and $H_2O$ approximately in the mole ratio of 1:6.1:1.66:4.3:750. Again the preferred growth condition was 4 days at 200° C.

Composition (2) was prepared by combining $V_2O_5$, V (325 mesh) $CH_3PO_3H_2$, $H_3PO_4$, $H_2N(CH_2)_2NH_2$ and $H_2O$ in a mole ratio of 0.95:1:2.79:7.33:6.73:1056 and heating the mixture for 4 days at 200° C. In particular, material (2) forms as dark blue, diamond-shaped plates with about an 80 per cent yield based on the total vanadium, and the by product was an amorphous white product.

Figure 5A:
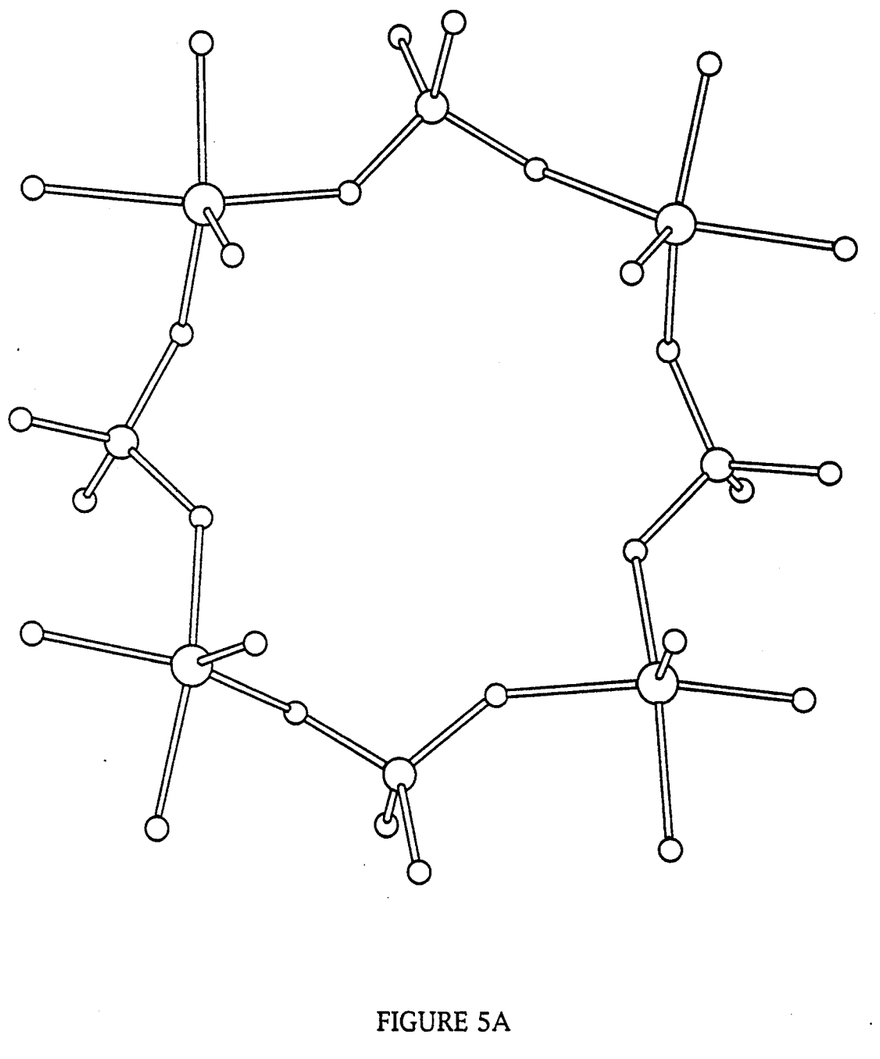
FIGS. 5A and 5B are views of the polyhedra ring building block of composition (2) that forms another example of the invention viewed parallel to and perpendicular to the plane of the ring, respectively.
Figure 5B:
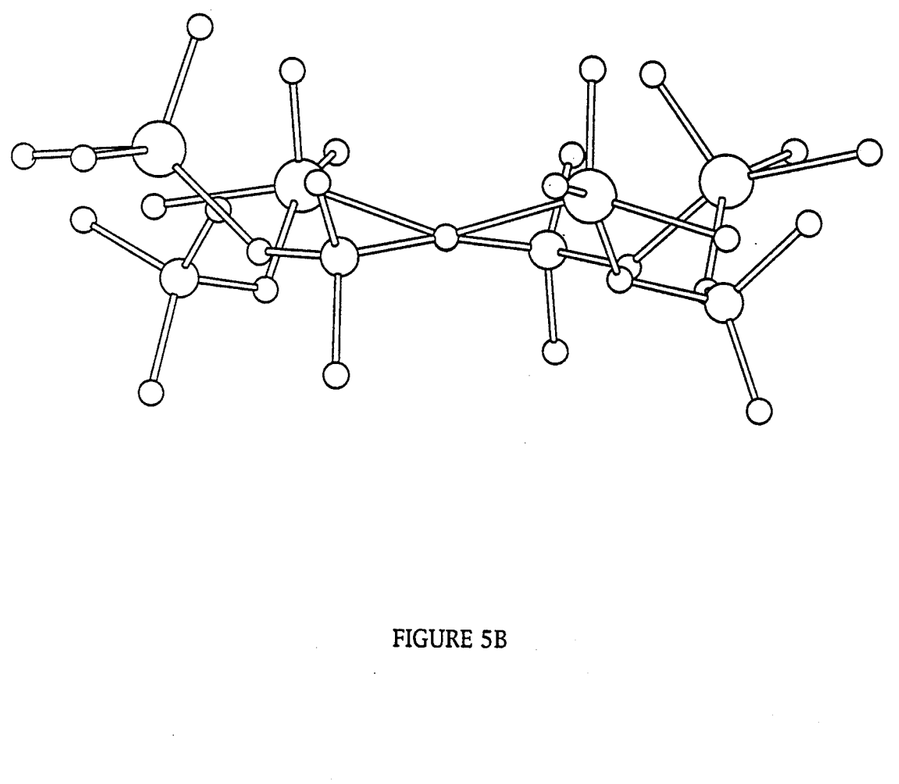

The structure of material (2) was also investigated by x-ray diffraction. The structure is constructed from corner-sharing V(IV) square pyramids, V(III) octahedra and $(PO_4)^{3-}$ and $(HPO_4)^{2-}$ tetrahedra and employs a number of structural motifs common to V—P—O phases. There are two types of binuclear V(IV) units in the V(IV)—P—O lamellar framework: $V_2(\mu_2-PO_4)_2$ and $V_2(\mu-OH)$ $(\mu_2-PO_4)$ groups. The overall structure may be grossly described as undulating layers, built up from corner sharing (via a $\mu_2$—OH group) V(IV) square pyramids and $HPO_4^{2-}$ and $PO_4^{3-}$ tetrahedra, connected together by V(III) octahedra. The fundamental building blocks of the layers are rings containing eight polyhedra: four $VO_5$ square pyramids, two $HPO_4^{2-}$ and two $PO_4^{3-}$ tetrahedra as shown in FIG. 5A. These rings are amphiphilic with the four less polar V=O vanadyl groups on one side of the plane defined by the V and P atoms and four P—O groups on the opposite face of the ring (FIG. 5B). Two of these P—O groups are strongly polar P—OH groups and two are P—O moieties that are bound to the interlamellar diaquo V(III) center. The layers are built up from these domed, amphiphilic rings. Each ring exhibits the V=O and P—OH groups in an anti orientation and is surrounded by six other rings: two with V=O up/P—OH down along b axis and four with V=O down/P—OH up. Within each layer, strips running along b axis formed from rings with the V=O up/P—OH down alternate with parallel stripx of V=O down/P—OH up. The two types of rings in the parallel strips are offset from one another by ½b. This up-down connectivity of the domed rings give rise to the undulations in the layers. The connectivity of the rings give rise to large holes (ca. 6.2 Å-7.2 Å atom to atom diameter) within the layers.

The three dimensional structure is formed by the connection of these layers through V(III) $(H_2O)_2$ centers. These V(III) atoms serve to produce elliptical cross sections in the large cavities by drawing together the polar regions of the layer while the nonpolar regions of the layers are pushed away from the organic cations. The atom-to-atom, V(III) to V(III), distance of the long axis of the elliptical channels is the unit cell length along the c axis of 18.4 Å. The polar $NH_3^+$ ends of the organic cations and the $H_2O$ of crystallization are situated within the cavities so as to maximize H-bonded interactions with the polar P—OH and $V(H_2O)_2$ portions of the framework while the less polar carbon backbones of the organic templates are associated with the V=O groups.

Composition (3) was prepared by reacting $VO_2$, $H_3PO_4$, $CH_3PO_3H_2$, 1,3 diaminopropane and $H_2O$ in approximately the following mole ratios 1:3:1:2.4:370. The reactants were heated for four days at about 200° C. to provide about a forty percent ratio of material (3) and side products. A sixty five percent yield was obtained by reacting $V_2O_5$, V, $H_3PO_4$, $CH_3PO_3H_2$, 1,3 diaminopropane and water in approximately the following mole ratios, 2.4:1:10:3.4:8.8:1390. Heating was done at 200° C. for 3 days.

Composition (4) was prepared in about 45 percent yield by reacting $KVO_3$, V, $H_3PO_4$, $CH_3PO_3H_2$, 1,3 diaminopropane and $H_2O$ in approxiately the following mole ratios 2.4:1:10:3.3:6.2:1250 for four days at 200° C.

As was earlier found in the case of the microporous molybdenum phosphates, hydrophilic-hydrophobic interactions appear to be an important factor in determining how this type of mixed organic-inorganic system can crystallize.

The successful incorporation of a relatively large organic template into a V—P—O solid phase characteristic of the invention demonstrates several emerging themes in the development of synthetic routes to such designed materials. Since the structures adopted by V—P—O phases are sensitive to the nature of the templates introduced, hydrophobic/hydrophilic interactions may be exploited in the self assembly of the frameworks by proper choice of templating inorganic and organic cations. Incorporation of both inorganic and organic cations into the V—P—O framework induces segregation of polar and nonpolar regions with the production of large incipient void volumes. Furthermore, V—P—O phases with 1:1 or lower V(IV,V):P ratios appear to be too polar to accommodate the organic template. Consequently, the introduction of reduced vanadium centers, specifically V(III), may provide a framework of reduced polarity, while dramatically expanding the structural chemistry of the system by providing the greater flexibility.

Accordingly, it should be understood that the specific vanadium phosphate compositions described are merely illustration of the general principles of our discovery, and that various modified versions of such materials can be prepared consistent with the principles described. In particular, from previous work with vanadium phosphate compositions, it can be expected that various other alkali and alkaline-earth metals can be substituted for the potassium in the potassium vanadium phosphates described.

What is claimed:

1. A composition having the formula in which A is one or more metals chosen from the group of alkali metals or alkaline-earth metals consisting of Li, Na, K, Rb, Cs, Mg, Ca, Sr, and Ba; B is an organic template of the form $R_4N$ in which R is one or more compositions chosen from the group consisting of H, $C_nH_{2n+1}$, $C_nH_{2n}NQ_3$ where n has a value equal to or less than 4 and Q is either H or $C_nH_{2n+1}$; and each of a and d has a value greater than zero, each of b, c, e, f, g, h, i, j, and x has a value equal to or greater than zero but at least one of g, h and i has a value greater than zero.

2. A composition in accordance with claim 1 having the formula $K_4[(CH_3)_2NH_2][V_{10}O_{10}(OH_4)(PO_4)_7(H_2O)_2] \cdot 4H_2O$ 3. A composition in accordance with claim 1 having the formula $[H_3NCH_2CH_2NH_3]_{2.5}[V(H_2O)_2V_8O_8(OH)_4(HPO_4)_4(PO_4)_4(H_2O)_2] \cdot 2H_2O$ 4. A composition in accordance with claim 1 having the formula $[H_3NCH_2CH_2CH_2NH_3][V_3O_3(OH)_2(PO_4)_2(H_2O)_2]$ 5. A composition in accordance with claim 1 having the formula $K[H_3NCH_2CH_2CH_2NH_3][V_3O_3(PO_4)_3]$ 6. A crystalline vanadium phosphate composition of matter that comprises, as determined by x-ray diffraction, a three-dimensional covalently-bonded framework built up of $VO_6$ octahedra, and/or $VO_5$ square pyramids and $PO_4$ tetra-hedra, where the connectivity of the covalently-bonded framework generates relatively small cavities and relatively large tunnels.

7. The composition of matter of claim 6 in which the tunnels house organic cations.

8. The composition of matter of claim 7 in which the cavities house inorganic cations.

9. The composition of matter of claim 6 in which the inorganic ions are potassium cations and the organic cations are dimethylammonium ions.

10. The composition of matter of claim 6 in which the inorganic cations are potassium ions and the organic cations are 1,3 diaminopropane ions.

11. The composition of matter of claim 6 in which the fundamental building blocks are two structurally similar crystallographically independent vanadium oxo pentamers arranged to form spirals with the spirals intertwined to form the two strands of a double helix with one strand composed of V1–V5 and the other strand composed of V6–V10.

12. The composition of matter of claim 11 in which the cavities include potassium cations and the tunnels include dimethylammonium cations.

13. A hydrothermal process for the self-assembly of a crystalline vanadium phosphate composition (1) that comprises the steps of heating at a temperature and for a time sufficient to form the composition a solution including essentially $KVO_3$, V, $H_3PO_4$, $CH_3PO_3H_2$, $(CH_3)_2NH$ and water, and then recovering the composition from the solution.

14. The process of claim 13 in which the precursors mentioned are in the solution approximately in the mole ratio of 2.35:1:10.2:3.3:8:1140 and the temperature is about 200° C. and the time is at least several days.

15. A hydrothermal process for the self assembly of a crystalline vanadium phosphate composition (2) that comprises the steps of heating at a temperature and for a time to form the composition from a solution including essentially $V_2O_5$, V, $CH_3PO_3H_2$, $H_3PO_4$, $H_2N(CH_2)_2NH_2$ and $H_2O$ and recovering the composition from the solution.

16. A hydrothermal process for the self assembly of a crystalline vanadium phosphate composition (3) that comprises the steps of heating for a time and at a temperature to form the composition from a solution including essentially $VO_2$, $H_3PO_4$, $CH_3PO_3H_2$, 1,3 diaminopropane and $H_2O$ and recovering the composition from the solution.

17. A hydrothermal process for the self assembly of a crystalline vanadium phosphate composition (4) that comprises the steps of heating for a time and at a temperature to form the composition from a solution including essentially $KVO_3$, V, $H_3PO_4$, $CH_3PO_3H_2$, 1,3 diaminopropane and $H_2O$, and recovering the composition from the solution.

* * * * *